United States Patent [19]

Koetsier et al.

[11] 4,435,608

[45] Mar. 6, 1984

[54] XYLENE ISOMERIZATION

[75] Inventors: Wicher T. Koetsier, Mijnsheerenland; Johannes P. Verduijn, Spijkenisse, both of Netherlands

[73] Assignee: Exxon Research & Engineering Co., Florham Park, N.J.

[21] Appl. No.: 327,176

[22] Filed: Dec. 4, 1981

[30] Foreign Application Priority Data

Dec. 12, 1980 [GB] United Kingdom ............. 8039961

[51] Int. Cl.³ ............................................ C07C 5/22
[52] U.S. Cl. .................................................. 585/480
[58] Field of Search ........................................ 585/480

[56] References Cited

U.S. PATENT DOCUMENTS

| | | | |
|---|---|---|---|
| 3,702,886 | 11/1972 | Argauer et al. | 423/328 |
| 3,790,471 | 2/1974 | Argauer et al. | 208/111 |
| 3,856,871 | 12/1974 | Haag et al. | 585/481 |
| 3,856,872 | 12/1974 | Morrison | 585/481 |
| 3,856,873 | 12/1974 | Burress | 585/481 |
| 3,941,871 | 3/1976 | Dwyer et al. | 423/326 |
| 4,061,724 | 12/1977 | Grose et al. | 423/335 |
| 4,073,865 | 2/1978 | Flanigen et al. | 423/339 |
| 4,104,294 | 8/1978 | Grose et al. | 260/448 |
| 4,148,713 | 4/1979 | Rullmann | 585/475 |
| 4,268,420 | 5/1981 | Klotz | 252/432 |
| 4,327,236 | 4/1982 | Klotz | 585/481 |

FOREIGN PATENT DOCUMENTS

| | | |
|---|---|---|
| 859656 | 2/1978 | Belgium . |
| 880858 | 2/1980 | Belgium . |
| 5909 | 12/1979 | European Pat. Off. . |
| 14059 | 6/1980 | European Pat. Off. . |
| 2023562 | 1/1980 | United Kingdom . |

OTHER PUBLICATIONS

Bibby et al., "Nature", vol. 280, pp. 664–665.

Primary Examiner—Curtis R. Davis
Attorney, Agent, or Firm—Rebecca Yablonsky

[57] ABSTRACT

Reduced downgrading in xylene isomerization of ethylbenzene-depleted feeds is achieved by carrying the process out over gallosilicate or borosilicate zeolites, preferably in the form of compositions comprising a core of catalytically-inactive crystalline silica with an overlying zeolite layer. The composites are prepared by introducing preformed silica particles, preferably with a crystallite size greater than $0.1\mu$, into a reaction mixture comprising a silicon source, a source of the modifying element, and preferably an organic template such as a tetraalkylammonium compound. The weight ratio of the silica core to $SiO_2$ in the reaction mixture is preferably 0.5:1 to 25:1.

6 Claims, 3 Drawing Figures

——— COMPARISON I     —·—·— EXAMPLE 5
——— EXAMPLE 2        ------- SILICALITE

FIG. 3.

XYLENE ISOMERIZATION

This invention relates to xylene isomerization of ethylbenzene-depleted feeds over a gallosilicate or borosilicate zeolite.

Zeolites have been known for some time as catalysts in hydrocarbon conversions. Naturally occuring zeolites are crystalline aluminosilicates with a characteristic porous structure made up of a three dimensional network of $SiO_4$ and $AlO_4$ tetrahedra cross-linked by shared oxygen atoms. Synthetic zeolites have been prepared with a variety of structures and aluminium contents, and in recent years zeolites have been prepared with particularly high silica contents, even to the extent of being substantially aluminium-free. In addition, zeolite structures have been synthesized with other elements replacing aluminium in the tetrahedral array.

The catalytic activity of zeolites relies on their acidity. Non-tetravalent atoms within the tetrahedral array, such as trivalent aluminium, gallium or boron, create a positive charge deficiency, which can be compensated by a cation such as $H^+$. In addition, the cavities and channels through the crystalline structure of the zeolite enable the materials to act as selective molecular sieves particularly if the dimensions of the channels fall within a range which enables the diffusion of large molecules to be controlled. Thus, acidic zeolites may be used as selective catalysts, and there are numerous publications describing such catalysts. By way of example, U.S. Pat. No. 3,790,471 describes a process for the isomerization of polyalkyl-substituted aromatics using an aluminosilicate zeolite identified as "ZSM-5" which is characterized by molar ratios of the constituent oxides and by its X-ray spectrum. The general formula for ZSM-5 disclosed therein embraces zeolites containing gallium and germanium, but only aluminosilicates are exemplified in the preparations for catalysts given in this U.S. Patent.

U.S. Pat. Nos. 3,856,871, 3,856,872 and 3,856,873 concern xylene isomerization processes which employ as the catalyst "zeolites of the ZSM-5 type, ZSM-12 or ZSM-21" for feeds containing xylenes and ethylbenzene. The process described employs an ethylbenzene tower upstream of the xylene recovery loop to strip some ethylbenzene from the feed while retaining all xylenes and without resorting to superfractionation. Thus, a significant amount of ethylbenzene remains in the feed to the isomerization—typically the feed contains 17 wt. % ethylbenzene. The ethylbenzene is destroyed by disproportionation and reaction with xylenes, but there are competing reactions including hydrode-alkylation and hydrocracking, and significant amounts of hydrocracked products, such as $C_{1-6}$ paraffins, are formed. It has now been found that by employing a gallosilicate or borosilicate zeolite, and recovering ethylbenzene within the recovery loop prior to isomerization, the amount of unwanted hydrocracking in the isomerization of the ethylbenzene-depleted feed is suprisingly reduced.

Accordingly, in one aspect this invention provides a process for obtaining ethylbenzene and para-xylene and/or ortho-xylene from a mixed $C_8$ feed, in which process ethylbenzene is recovered from the mixed $C_8$ feed to leave an ethylbenzene-depleted feed containing mixed xylenes and less than 5 wt % ethylbenzene, the ethylbenzene-depleted feed is thereafter contacted under isomerization conditions and a catalyst comprising a zeolite containing a modifying element W within the tetrahedral zeolite structure wherein W represents at least one of Ga and B, having a mole ratio of $SiO_2$:$W_2O_3$ greater than 5 and a constraint index (as defined hereinafter) of from 1 to 12 to give an isomerate enriched in para-xylene and ortho-xylene, and para-xylene and/or ortho-xylene are recovered from the isomerate which is thereafter recycled to the ethylbenzene recovery step.

The zeolite may be a gallosilicate, a borosilicate or a gallo/borosilicate, and is preferably substantially free of tetrahedral aluminium. Preferably the ratio of silicon to aluminium in the tetrahedral framework of the gallo and/or borosilicate is greater than 5000. The zeolite preferably has a mole ratio of $SiO_2$:$W_2O_3$ of greater than 12.

The "constraint index" is a measure of the degree of access of larger molecules to the zeolite and may be determined by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° and 950° F. (287° and 510° C.) to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analysed, most conveniently by gas chromatography, to determine the fraction remaining unchanged for each of the two hydrocarbons. The "constraint index" is calculated as follows:

$$\text{Constraint Index} = \frac{\log_{10} (\text{fraction of n-hexane remaining})}{\log_{10} (\text{fraction of 3-methylpentane remaining})}$$

Preferably the zeolite has a formula (expressed in terms of mole ratios of oxides) as follows:

$$M_{2/n}O:W_2O_3:YSiO_2:zH_2O$$

wherein M is at least one cation of valence n, W is Ga and/or B, Y is at least 5 and preferably at least 12, and most preferably from 20 to 5000, and z is from 0 to 40.

The zeolite preferably has an X-ray diffraction pattern characteristic of the ZSM-5 family, as defined in U.S. Pat. No. 3,702,886. A preferred gallosilicate zeolite is described in GB No. 2,023,562. A preferred borosilicate is that described in BE No. 859656 or BE No. 880858. The gallosilicate or borosilicate may be prepared by crystallisation from a reaction mixture comprising a silica source, a source of $Ga_2O_3$ or $B_2O_3$ and optionally an organic template compound. The preparation of the zeolites is believed to be within the competence of one skilled in the art, and is described for example in the patents describing the preferred zeolites.

It has been found that a surprisingly effective acidic zeolite catalyst may be obtained by applying a gallo- and/or borosilicate zeolite to a crystalline silica core which has few acid sites and therefore limited catalytic properties per se. Moreover, the resultant composite zeolite catalyst has been found to display advantages in the process of the invention when compared to the gallo- and/or borosilicate alone or to the silica alone.

Accordingly, the catalyst is preferably a composition comprising the gallo- and/or borosilicate zeolite overlying a silica core, the silica core and the zeolite have substantially the same crystalline structure. The silica core may be a silica polymorph of analogous structure to a zeolite or a highly siliceous zeolite, having in each case substantially free of metal or non-metal substitution within the silica framework. Preferred forms of the silica core are polymorphs or zeolites in which the ratio of silicon to modifying elements in the tetrahedral framework is greater than 500, and more preferably greater than 5000 and approaches infinity. The composition for use in the invention comprises a silica core and an overlying modified-silica zeolite having substantially the same crystalline structures, and thus the silica core and the complete composite catalyst preferably display substantially the same X-ray diffraction patterns.

The core may, for example, be a crystalline silica polymorph which has, after calcination in air for at least one hour at 600|C., a mean refractive index of 1.39±0.01 and a specific gravity at 25|C. of 1.70±0.05.

In one preferred form the polymorph has an X-ray powder diffraction pattern in which the six strongest d-values are:

11.1±0.2 Å
10.0±0.2 Å
3.85±0.07 Å
3.82±0.07 Å
3.76±0.05 Å
3.72±0.05 Å

This silica polymorph, known as "Silicalite", is described in U.S. Pat. No. 4,061,724 assigned to Union Carbide Corporation.

The pore diameter of Silicalite is about 6 Å and the pore volume is typically 0.18 ml/g determined by adsorption.

Silicalite may be prepared by the process described in U.S. Pat. No. 4,061,724 which consists of a hydrothermal crystallization from an aqueous reaction mixture containing a silica source and an alkonium compound of pH 10-14 to form a hydrous precursor, followed by calcining the precursor. However, Silicalite may alternatively be prepared by a generally similar process but in the absence of alkonium compounds.

A second preferred form of silica polymorph related to Silicalite has, in addition to the refractive index and specific gravity characteristics given above, following calcination in air for at least one hour at 600° C. an adsorptive capacity for water vapours at 23° C. and a water vapour pressure of 4.6 mm Hg of less than 1 wt %, an infra-red spectrum which exhibits a substantial absence of absorption in the region 3700-3100 cm$^{-1}$, and an X-ray powder diffraction pattern containing at least the following d-values:

11.1±0.2 Å
10.0±0.2 Å
9.75±0.1 Å
3.85±0.04 Å
3.82±0.04 Å
3.71±0.02 Å
3.62±0.02 Å and an absence of reflections intermediate the reflections corresponding to d-spacing of 3.82±0.04 Å and 3.71±0.02 Å.

This second form of preferred silica polymorph is described and claimed in U.S. Pat. No. 4,073,865 assigned to Union Carbide Corporation. The polymorph may be prepared by the process as described in U.S. Pat. No. 4,073,865, which employs a reaction mixture having a pH below 11, preferably within the range 7 to 11, more preferably 7.4 to 10, which reaction mixture contains from 150 to 1500 moles $H_2O$, from 13 to 50 moles $SiO_2$, from 2 to 12 moles of fluoride ion and from 0 to 20 moles, preferably from 0 to 6 moles, of $M_2O$ wherein M represents an alkali metal cation, each of the aforesaid reagents being present per mole of $Q_2O$ wherein Q represents a quaternary cation having the formula $(R_4X)^+$, in which each R represent hydrogen or an alkyl group containing from 2 to 6 carbon atoms, and X represents phosphorus or nitrogen. The reaction mixture is heated at a temperature of from 100° C. to 250° C. until a crystalline hydrated precursor is formed, usually after about 50 to 150 hours, then the crystalline precursor is isolated and calcined at a temperature of from 400° C. to 1000° C. The silica polymorph may, however, alternatively be prepared in the absence of the compound $Q_2O$.

The core may also be the silicate resulting from thermal treatment at a temperature of from 200° C. to 600° C. for from 1 to 48 hours of a crystal metal organosilicate having a composition, in its anhydrous state, in terms of mole ratios of oxides as follows:

$0.9\pm0.2(xR_2O+(1-x)M_{2/n}O): <0.005Al_2O_3: >1\text{-}SiO_2$ where M is sodium or sodium in combination with tin, calcium, nickel or zinc, R is a tetraalkylammonium and x is a number greater than 0 but not exceeding 1, the organosilicate having the characteristic X-ray diffraction lines of the ZSM-5 zeolite—that is to say:

| Interplanar spacing d (Å) | Relative Intensity |
|---|---|
| 11.1 ± 0.2 | s |
| 10.0 ± 0.2 | s |
| 7.4 ± 0.15 | w |
| 7.1 ± 0.15 | w |
| 6.3 ± 0.1 | w |
| (6.04) | |
| 0.1 | w |
| (5.97) ± | |
| 5.56 ± 0.1 | w |
| 5.01 ± 0.1 | w |
| 4.60 ± 0.08 | w |
| 4.25 ± 0.08 | w |
| 3.85 ± 0.07 | vs |
| 3.71 ± 0.05 | s |
| 3.04 ± 0.03 | w |
| 2.99 ± 0.02 | w |
| 2.94 ± 0.02 | w |

A silica of this type is described and claimed in U.S. Pat. No. 3,941,871 assigned to Mobil Oil Corporation.

The silica core may also be a crystalline silica having the characteristic X-ray diffraction pattern of the zeolite ZSM-11:

| Interplanar spacing d (Å) | Relative Intensity |
|---|---|
| 11.2 ± 0.2 | m |
| 10.1 ± 0.2 | m |
| 6.73 ± 0.2 | w |
| 5.75 ± 0.1 | w |
| 5.61 ± 0.1 | w |
| 5.03 ± 0.1 | w |

| Interplanar spacing d (Å) | Relative Intensity |
|---|---|
| 4.62 ± 0.1 | w |
| 4.39 ± 0.08 | w |
| 3.86 ± 0.07 | vs |
| 3.73 ± 0.07 | m |
| 3.49 ± 0.07 | w |
| (3.07) ± 0.05 | w |
| (3.00) | |
| 2.01 ± 0.02 | w |

The parenthesis around lines 3.07 and 3.00 indicate that they are separate and distinct lines, but are often superimposed. The ZSM-11 X-ray diffraction pattern is similar to that of ZSM-5, except that the lines at interplanar spacings of 10.1, 3.73, 3.00 and 2.01 A are singlets rather than doublets as in the case of ZSM-5.

A silica polymorph having the ZSM-11 X-ray spectrum is described in an article by D. M. Bibby et al. in "Nature" vol. 280, pages 664–665. This silica polymorph, there called "silicalite-2", is prepared by reacting a silica source with tetra-n-butylammonium hydroxide, and optionally ammonium hydroxide or hydrazine hydrate, at 100° C. to 200° C. to form a precursor, which in turn decomposes at 300° C. to yield silicalite-2.

A ZSM-11 with very low aluminium content is also described and claimed in published European Application No. 14059 in the name of Mobil Oil Corporation as a composition (in terms of moles of oxide) of:

$(0-10)M_{2/n}O: <0.5Al_2O_3:100SiO_2$ in which M is a cation of valence n.

A further possibility is that the crystalline silica component of the catalyst is a silica polymorph having the following significant lines in its X-ray pattern:

| Interplanar spacing d (Å) | Relative Intensity |
|---|---|
| 11.9 ± 0.2 | s |
| 10.2 ± 0.2 | m |
| 4.76 ± 0.1 | w |
| 4.29 ± 0.08 | vs |
| 3.87 ± 0.07 | vs |
| 3.66 ± 0.07 | w |
| 3.49 ± 0.07 | w |
| 3.38 ± 0.07 | m |
| 3.20 ± 0.06 | w |
| 3.05 ± 0.05 | w |
| 2.64 ± 0.03 | w |

A silica core of this type may be obtained, for example, by calcination of an organosilicate as described and claimed in U.S. Pat. No. 4,104,294, assigned to Union Carbide Corporation.

The proportion of the two components of the catalyst—silica core and gallosilicate or borosilicate zeolite—are preferably chosen so that the mean ratio of silicon to gallium or boron in the composite zeolite (expressed in terms of mole ratios of their oxides) is not less than 7.5, preferably from 15 to 20,000, and most preferably from 20 to 500.

The composite zeolite may be prepared by a process in which formed crystalline silica particles are placed in a crystallisation gel for a zeolite composition comprising a silica source, a source of gallium or boron, and optionally an organic template molecule, and the crystallization gel is maintained under appropriate reaction conditions to bring about formation on the silica particles of gallo- and/or borosilicate, the silica and the modified-silica zeolite having substantially the same crystalline structure.

The preparation of the silica particles which ultimately form the core of the composite zeolite is believed to be within the competence of one skilled in the art. For example, one may use the processes described in U.S. Pat. Nos. 4,061,724, 4,073,865, 3,941,871, 4,104,294, European Application No. 14059 and the Bibby et al. article in "Nature", Vol. 280, pages 664–665.

The gallosilicate or borosilicate zeolite shell may be formed in the manner described in the patents indicated hereinbefore in relation to the preferred zeolites. It is believed to be within the competence of one skilled in the art to select crystallisation conditions appropriate for the crystal structure required for the shell. By way of illustration, it is pointed out that the gallo- and/or borosilicate may be formed upon the silica core using the following techniques. A silica source, which may be a hydrated silica or colloidal silicon oxide solution, is mixed with a solution of an organic template, such as an alkonium compound. The source of gallium or boron, preferably as an oxide, and an alkali, such as sodium hydroxide, are then added. To this solution the preformed particles of the silica core are added, and the whole is then subjected to heating for an appropriate time to bring about crystallisation of the zeolite on the silica core. The crystallisation typically is carried out at from 100° to 200° C. for from 1 to 30 days.

After crystallisation the product may be washed, dried and heated to destroy any organic compounds. The catalyst may then be contacted with a solution of an ammonium compound to replace cations by $NH_4^+$ which may then be destroyed by calcination, leaving protons at the acid sites to provide the Bronsted acidity of the catalyst. The calcination steps are preferably carried out at a temperature of from 400° to 600° C. and most preferably 400° to 450° C.

The zeolite preferably has the same crystalline structure as the silica core on which it is formed. Thus, the zeolite and the silica core preferably show the same characteristic lines in their X-ray powder diffraction spectra. It is highly preferred for the zeolite and the silica core to show the same characteristic X-ray pattern as the ZSM-5 zeolite described and claimed in U.S. Pat. No. 3,702,886.

The catalyst of the invention may be formed in a range of crystallite sizes, but it is preferred to employ a silica core of greater than $0.1\mu$ mean diameter. Most preferably the silica core has a mean diameter of from $0.5\mu$ to $20\mu$. The complete catalyst has the zeolite formed on the outer surface of the silica core, and this may form a partial or complete layer over the core, or be in the form of discrete particles on the core surface. Scanning electron micrographs show that these catalysts form composite crystallites of similar size to the silica core used, but with a "rough" surface which is believed to result from the formation of the modified silica layer. Surprisingly, it has been found that even only very small amounts of zeolite produce a catalyst with good activity, even though the silica core itself is substantially inactive.

Preferably the weight ratio of the silica core to the overlying zeolite (expressed in terms of the weight ratio of the $SiO_2$ core to the $SiO_2$ in the reaction mixture for the modified-silica) is from 0.5:1 to 25:1, and more preferably from 1:1 to 10:1 and most preferably from 1:1 to 4:1.

The process of the invention employs recovers ethylbenzene from a $C_8$ feed to give an ethylbenzene depleted feed. A $C_8$ feed will contain ethylbenzene and mixed xylenes (that is, ortho-xylene, meta-xylene and para-xylene). The proportions of these various components will vary depending upon the source of the $C_8$ feed. Typically, however, a $C_8$ feed derived from petroleum naphtha will contain from 10 to 32 wt % ethylbenzene, the balance being mixed xylenes in the approximate proportion of 50% meta-xylene, 25 wt % ortho-xylene and 25 wt % para-xylene. According to the invention, the following ethylbenzene recovery, the resulting ethylbenzene-depleted feed contains less than 5 wt % ethylbenzene, preferably less than 4 wt % ethylbenzene. Complete ethylbenzene removal is extremely difficult and a practical a lower limit for ethylbenzene content is 1 wt %.

Preferably the ethylbenzene is removed to produce the ethylbenzene-depleted feed by means of super-fractionation or an adsorption process, for example using a molecular sieve.

The ethylbenzene-depleted feed is then contacted with the catalyst to isomerize the xylenes to produce an isomerate enriched in para-xylene.

The isomerization reaction may be carried out under conventional conditions for zeolite catalysed xylene isomerization, either in liquid or vapour phase, optionally in the presence of hydrogen. In the liquid phase the preferred conditions are:

Temperature (|C.): 150–270
Pressure (bar): 1–100
WHSV: 0.1–10

In the vapour phase the isomerization is preferably carried out in the presence of hydrogen under the following conditions:

Temperature (|C.): 220–400
Pressure (bar): 1–100
WHSV: 0.1–100
Molar ratio, $H_2$:Hydrocarbon: 0.1–10.

The isomerate enriched with ortho-xylene and para-xylene and one or both of these xylenes is then recovered. Ortho-xylene may be separated by fractional distillation. The isomerate may be fed to a xylene splitter, and the bottoms (containing ortho-xylene and $C_8$ aromatics) may then be passed to an ortho-xylene tower, in which orthoxylene is taken overhead.

Para-xylene is usually recovered either by fractional crystallization or by adsorption, and such techniques are well known in the art.

Normally both ortho-xylene and para-xylene will be recovered from the isomerate, but the order in which these two xylenes are recovered is immaterial.

Following such recovery the isomerate is recycled to the ethylbenzene recovery step, and thus a closed xylene loop is formed. Fresh $C_8$ feed is introduced into the loop and the point of its introduction is not critical provided, of course, that the ethylbenzene containing feed is not introduced between the ethylbenzene recovery and the isomerization unit.

Certain aspects of the invention will now be described in more detail with reference to the accompanying drawings, in which.

Figure 3:
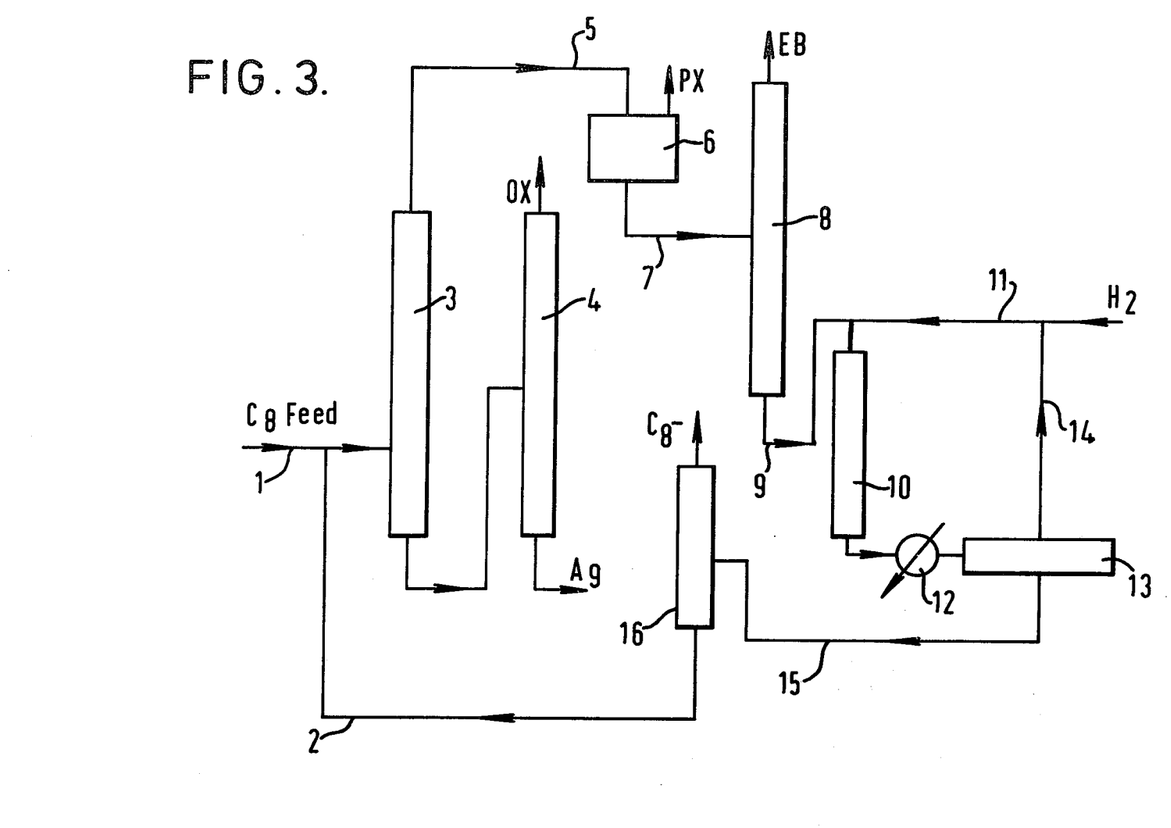
FIG. 3 is a flow diagram of a process of the invention.

As shown in FIG. 3 a $C_8$ feed containing ethylbenzene and mixed xylenes is introduced into a xylene loop by line 1. This feed together with isomerate recycled via line 2 is fed to a xylene splitter tower 3 from which bottoms containing ortho-xylene and $C_8$ aromatics are fed to the ortho-xylene tower 4 where the ortho-xylene is recovered as overhead.

The overhead from tower 3 is fed via line 5 to the para-xylene recovery unit 6, which may be a fractional crystallizer or an adsorption unit, from which para-xylene is recovered. The residue which is rich in ethylbenzene is then fed via line 7 to ethylbenzene tower 8, where by superfractionation the ethylbenzene content of the feed is reduced to 5 wt % or less. Alternatively, a molecular sieve adsorption process may be used in place of tower 8.

The ethylbenzene-depleted feed is fed via line 9 and a heater (not shown) to the isomerization unit 10. Where hydrogen is required this is introduced into the feed via line 11. In unit 10 the feed (and hydrogen when appropriate) is contacted with the borosilicate and/or gallosilicate catalyst under isomerization conditions to form an isomerate enriched in ortho and para-xylene which is cooled in heat exchange 12. When hydrogen is used in the isomerization this is separated in separator 13 and recycled via line 14. The isomerate is fed via line 15 to a stripper 16 which removes light ends and the bottoms from the stripper is recycled via line 2.

The following Examples and Test Results are now given, though only by way of illustration, to show certain aspects of the invention in more detail.

EXAMPLES 1–5

Preparation of Composite Catalyst

A. Preparation of silica core 476 g of silica (as Ludox HS-40 a commercially available colloidal silica) were diluted with 100 ml of water. The formed solution was mixed with 130 ml 20% TPA-OH (by weight) tetrapropylammonium salt solution. To this mixture was added a solution of 33 g NaOH in 100 ml water so as to form a synthesis gel. The gel was placed in two 250 ml polypropylene bottles provided with condensers which were heated in an oil bath for 7 days at 100° C. to bring about crystallisation. After the crystallisation period the crystalline core material was collected, washed and dried.

The core material obtained according to the above procedure had a very strong X-ray diffraction pattern, the d-values of which are shown in Table 1 below, along with those for Union Carbide Corporation's silicalite (the reduction of the X-ray spectrometer does not enable all the lines defined in U.S. Pat. No. 4,061,724 to be identified). Scanning Electron Photomicrographs showed spherically-shaped crystal aggregates with a particle size of 0.5 micron.

B. Preparation of composite catalyst

The general procedure adopted was as follows. Hydrated silica ($SiO_2.nH_2O$) was mixed with a hot 20% (by weight) solution of tetrapropylammonium salt for 5 minutes (solution 1).

TABLE 2-continued

| | | | | | |
|---|---|---|---|---|---|
| 5 | 4 | 170 | 9.0 | 0.006 | 0.006 |

(1) Silica polymorph available from Union Carbide Corporation.
(2) Silica prepared as in Step A.
(3) Mixture of Silicalite and silica from Step A in the weight ratio 3:2.

TABLE 3

| Example | pH REACTANT MIXTURE before synthesis | pH REACTANT MIXTURE after synthesis | DRIED WEIGHT grams | PRECALCINATION IN AIR time hrs | PRECALCINATION IN AIR temp °C. | PRECALCINATION IN AIR wt loss % | NH4 EXCHANGE time hrs | NH4 EXCHANGE temp °C. | FINAL CALCINATION IN AIR time hrs | FINAL CALCINATION IN AIR temp °C. | FINAL CALCINATION IN AIR wt loss % |
|---|---|---|---|---|---|---|---|---|---|---|---|
| I | | | 42 | 16 | 400 | | 2 | 90 | 16 | 400 | |
| 1 | 13.5 | 13.1 | 28.6 | 16 | 400 | 14.5 | 2 | 90 | 16 | 400 | 1.7 |
| 2 | 13.5 | 12.8 | 19.6 | 16 | 400 | 3.9 | 2 | 90 | 16 | 400 | 1.2 |
| 3 | 13.8 | 13.2 | 14.9 | 16 | 400 | 11.3 | 2.5 | 90 | 18 | 400 | 1.3 |
| 4 | 13.9 | 13.3 | 26.9 | 16 | 400 | 12.1 | 2.5 | 90 | 18 | 400/475 | 1.1/1.6 (1) |
| 5 | 13.8 | | 36.8 | 16 | 400 | 12.4 | 2.5 | 90 | 18 | 400/475 | 1.1/1.3 (1) |

(1) The products of Examples 5 and 6 were split in three portions, one left uncalcined (after exchange), the second and third portions were calcined at 400 to 475° C. respectively.

TABLE 4

| CATALYST | ELEMENTAL ANALYSIS Si % | ELEMENTAL ANALYSIS Na ppm | ELEMENTAL ANALYSIS B ppm | ELEMENTAL ANALYSIS Ga % | ELEMENTAL ANALYSIS Al % | ACIDITIES (1) Bronsted | ACIDITIES (1) Lewis | X-RAY DIFFRACTION | SEM PICTURES Crystal shape | SEM PICTURES Crystal size (μ) | OVERALL METAL/SILICONE ATOMIC Ratio | REMARKS |
|---|---|---|---|---|---|---|---|---|---|---|---|---|
| I | 42.1 | 12 | — | — | 1.3 | 570 | 130 | ZSM-5 | spherical | 10 | 0.032 | |
| 1 | 45.9 | 95 | 1500 | — | — | 160 | 65 | ZSM-5 | spherical | 10 | 0.008 | |
| 2 | 44.5 | 95 | — | 2.1 | — | 135 | 89 | ZSM-5 | spherical | 10 | 0.019 | |
| 3 | 45.3 | 125 | — | 2.11 | — | 90 | 20 | ZSM-5 | spherical | 0.5 | 0.019 | |
| 4/1 | 45.8 | 35 | — | 1.2 | — | 80 | 55 | ZSM-5 | spherical | 0.5 | 0.011 | (2) |
| 4/2 | | | | | | 55 | 65 | | | | | |
| 5/1 | 45.9 | 45 | — | 0.7 | — | 70 | 55 | ZSM-5 | spherical | 0.5 | 0.006 | (3) |
| 5/2 | | | | | | 70 | 45 | | | | | |
| II | 42.7 | 1 | — | — | 0.88 | 150 | 105 | ZSM-5 | irregular | 10 | 0.043 | |

(1) μ mol lutidine/pyridine retention per gram catalyst at 300° C. after 10 minutes.
(2) Example 5/1 calcined at 400° C., Example 5/2 calcined at 475° C.
(3) Example 6/1 calcined at 400° C., Example 6/2 calcined at 475° C.

TABLE 5

X-ray pattern of the catalyst of Example 4

| 2θ (degrees) | d (Å) | Intensity |
|---|---|---|
| 8.00 | 11.05 | vs |
| 8.95 | 9.88 | vs |
| 12.00 | 7.38 | vw |
| 12.55 | 7.05 | vw |
| 13.30 | 6.66 | w |
| 14.05 | 6.30 | w |
| 14.90 | 5.95 | m |
| 15.75 | 5.63 | m |
| 16.00 | 5.54 | vw |
| 16.70 | 5.31 | vw |
| 17.35 | 5.11 | vw |
| 17.85 | 4.97 | w |
| 18.35 | 4.83 | vw |
| 18.80 | 4.72 | vw |
| 19.35 | 4.59 | w |
| 20.45 | 4.34 | w |
| 20.95 | 4.24 | w |
| 21.85 | 4.07 | vw |
| 22.30 | 3.99 | w |
| 23.25 | 3.83 | w |
| 24.00 | 3.71 | s |
| 24.50 | 3.63 | m |
| 25.70 | 3.47 | w |
| 26.00 | 3.43 | vw |
| 26.80 | 3.33 | w |
| 27.00 | 3.30 | vw |
| 27.50 | 3.24 | vw |
| 28.25 | 3.16 | vw |
| 28.55 | 3.13 | vw |
| 29.40 | 3.04 | w |
| 30.10 | 2.97 | w |
| 31.30 | 2.86 | vw |
| 32.20 | 2.78 | vw |
| 32.35 | 2.77 | vw |
| 32.90 | 2.72 | vw |
| 33.35 | 2.69 | vw |
| 33.55 | 2.67 | vw |
| 33.80 | 2.65 | vw |
| 34.00 | 2.64 | vw |
| 34.55 | 2.60 | vw |
| 35.90 | 2.50 | vw |
| 36.20 | 2.48 | vw |
| 37.35 | 2.41 | vw |
| 37.60 | 2.39 | vw |

Test Results

The performance of the five examples of composite catalysts comprising gallosilicate or borosilicate was compared against comparison catalyst I defined hereinbefore, pure silicalite (available from Union Carbide Corporation) and a conventional aluminosilicate ZSM-5 (referred to hereinafter as comparison catalyst II). Comparison catalyst II was prepared by the technique described in Step B above but without the addition of core material. Details of comparison catalyst II are given in Table 4.

The catalysts were tested for the following reactions.

Sodium hydroxide and a source of the modifying element W were dissolved in water (solution 2) and solutions 1 and 2 were mixed for 5 minutes. In Examples 2, 4 and 5 where W was gallium a different procedure was employed: $Ga_2O_3$ was not dissolved in sodium hydroxide, but $Ga_2O_3$ power and sodium hydroxide solution added to solution 1.

The core material (prepared as in Step A and/or commercially available silicalite from Union Carbide Corporation) was then added with water and the whole was mixed for 5 minutes to form a slurry. After pH measurement, the slurry was placed in a Teflon coated autoclave and put in an oven at autogenous pressure.

After crystallisation the product was washed several times, dried at 120|C and precalcined to destroy organic compounds. The product was then ammonia exchanged to replace sodium by $NH_4+$ and again calcined to decompose the $NH_4+$ leaving protons to provide Bronsted acidity.

Details of the amounts of reactant used, the nature of the reactants, the proportion of zeolite to inert silica core and the crystallisation conditions are given in Table 2.

The ion exchange and calcination conditions are given in Table 3. Results are also given for a composite catalyst having an aluminosilicate shell to provide, a comparison; this comparison catalyst is designated hereinafter I.

The properties of the catalysts are summarized in Table 4. An example of an X-ray pattern is given in Table 5 for the catalyst of Example 4.

TABLE 1

| Silica polymorph prepared in Step A | | | Silicalite | | |
|---|---|---|---|---|---|
| 2θ (degrees) | d (Å) | Intensity | 2θ (degrees) | d (Å) | Intensity |
| 7.85 | 11.26 | vs | 7.85 | 11.26 | vs |
| 8.75 | 10.11 | vs | 8.85 | 9.98 | vs |
| 10.85 | 8.15 | vw | 11.85 | 7.47 | vw |
| 11.80 | 7.50 | vw | 13.15 | 6.73 | m |
| 12.00 | 7.38 | vw | 13.90 | 6.37 | m |
| 12.50 | 7.08 | vw | 14.80 | 5.00 | s |
| 12.70 | 6.97 | vw | 15.50 | 5.72 | m |
| 13.15 | 6.73 | w | 15.90 | 5.57 | m |
| 13.85 | 6.39 | w | 16.50 | 5.37 | w |

TABLE 1-continued

| Silica polymorph prepared in Step A | | | Silicalite | | |
|---|---|---|---|---|---|
| 2θ (degrees) | d (Å) | Intensity | 2θ (degrees) | d (Å) | Intensity |
| 14.70 | 6.03 | m | 17.35 | 5.11 | vw |
| 15.50 | 5.72 | w | 17.70 | 5.01 | m |
| 15.80 | 5.61 | m | 18.15 | 4.89 | vw |
| 16.45 | 5.39 | vw | 19.20 | 4.62 | w |
| 17.15 | 5.17 | vw | 19.90 | 4.46 | vw |
| 17.70 | 5.01 | w | 20.45 | 4.34 | w |
| 19.20 | 4.62 | w | 20.80 | 4.27 | m |
| 20.30 | 4.37 | w | 21.75 | 4.08 | vm |
| 20.75 | 4.28 | w | 22.20 | 4.00 | w |
| 21.75 | 4.09 | vw | 23.00 | 3.87 | vs |
| 22.10 | 4.02 | w | 23.35 | 3.31 | vs |
| 23.05 | 3.86 | vs | 23.70 | 3.75 | s |
| 23.85 | 3.73 | s | 23.90 | 3.72 | vs |
| 24.35 | 3.66 | m | 24.40 | 3.65 | s |
| 25.75 | 3.46 | w | 25.55 | 3.49 | w |
| 26.50 | 3.36 | vw | 25.85 | 3.45 | w |
| 26.85 | 3.32 | w | 26.25 | 3.39 | w |
| 27.30 | 3.27 | vw | 26.60 | 3.35 | w |
| 28.20 | 3.16 | vw | 26.85 | 3.32 | m |
| 29.25 | 3.05 | w | 27.40 | 3.25 | w |
| 29.85 | 2.99 | w | 28.10 | 3.18 | vw |
| 31.10 | 2.88 | vw | 28.40 | 3.14 | vw |
| 32.70 | 2.74 | vw | 29.95 | 2.98 | m |
| 33.45 | 2.68 | vw | 30.25 | 2.95 | w |
| 34.30 | 2.61 | vw | 31.20 | 2.87 | vw |
| 34.45 | 2.60 | vw | 32.75 | 2.73 | vw |
| 34.65 | 2.59 | vw | 33.40 | 2.68 | vw |
| 34.90 | 2.57 | vw | 33.75 | 2.66 | vw |
| 36.15 | 2.48 | vw | 34.40 | 2.61 | vw |
| 37.40 | 2.40 | vw | 35.00 | 2.56 | vw |
| 45.10 | 2.01 | vw | 35.70 | 2.51 | vw |
| 45.45 | 2.00 | vw | 36.10 | 2.49 | vw |
| 46.40 | 1.96 | vw | 37.20 | 2.42 | vw |
| 47.40 | 1.92 | vw | 37.50 | 2.40 | vw |
| 48.60 | 1.87 | vw | 43.50 | 2.08 | vw |
| | | | 45.15 | 2.01 | w |
| | | | 45.50 | 1.99 | w |
| | | | 46.45 | 1.95 | vw |
| | | | 47.50 | 1.91 | vw |
| | | | 48.75 | 1.87 | vw |
| | | | 51.98 | 1.76 | vw |
| | | | 55.00 | 1.67 | vw |
| | | | 55.20 | 1.56 | vw |
| | | | 62.35 | 1.49 | vw |
| | | | 63.65 | 1.46 | vw |
| | | | 64.60 | 1.45 | vw |
| | | | 67.15 | 1.39 | vw |

TABLE 2

| EXAMPLE | REACTANTS FOR SHELL | | | | INERT CORE | MOLE RATIOS OF REACTANTS | | | |
|---|---|---|---|---|---|---|---|---|---|
| | template form | cation | metal source | silicon source | | Metal/Si | $H_2O$/$SiO_2$ | $H_2O$/$OH^-$ | TPA/(TPA + NA) |
| I | TPA—BR | Na | $NaAlO_2$ | Ludox LS30 | Silicalite (1) | 0.08 | 17 | 22 | 0.5 |
| 1 | TPA—OH | Na | $H_3BO_3$ | $SiO_2$—$nH_2O$ | Silicalite (3) +A | 0.10 | 34 | 56 | 0.6 |
| 2 | TPA—OH | Na | $Ga_2O_3$ | $SiO_2$—$nH_2O$ | Silicalite | 0.06 | 36 | 57 | 0.6 |
| 3 | TPA—OH | Na | $Ga_2O_3$ | $SiO_2$—$nH_2O$ | A (2) | 0.06 | 34 | 51 | 0.6 |
| 4 | TPA—OH | Na | $Ga_2O_3$ | $SiO_2$—$nH_2O$ | A | 0.06 | 34 | 51 | 0.6 |
| 5 | TPA—OH | Na | $Ga_2O_3$ | $SiO_2$—$nH_2O$ | A | 0.06 | 34 | 51 | 0.6 |

| EXAMPLE | CRYSTALLISATION | | Wt. RATIO CORE/modified silica | OVERALL METAL/SILICON ATOMIC RATIOS | |
|---|---|---|---|---|---|
| | time days | temp |C. | | expected | actual |
| I | 7 | 175 | 1.5 | 0.04 | 0.032 |
| 1 | 7 | 150 | 4.6 | 0.018 | 0.008 |
| 2 | 4 | 175 | 3.0 | 0.015 | 0.019 |
| 3 | 4 | 170 | 3.0 | 0.015 | 0.019 |
| 4 | 4 | 170 | 6.0 | 0.009 | 0.011 |

(a) Xylene isomerization

The two xylene isomerization reactions are given by the following two equations:

$$MX \rightleftharpoons PX \quad (1)$$

$$MX \rightleftharpoons OX \quad (2)$$

MX=meta-xylene, PX=para-xylene, OX=ortho-xylene.

The activity of the catalyst for xylene isomerization is expressed as the approach to equilibrium:

$$PX\text{-Approach to EQM} = \frac{\frac{PX}{\text{total } X}\text{(in feed)} - \frac{PX}{\text{total } X}\text{(in product)}}{\frac{PX}{\text{total } X}\text{(in feed)} - \frac{PX}{\text{total } X}\text{(at eqm)}} \times 100\%$$

For the OX-Approach to EQM a similar definition is used.

(b) Ethylbenzene Reduction

The Ethylbenzene Reduction (EBR) is caused by the following four reactions:

$$\text{transalkylation: } EB + X \rightleftharpoons Me\text{-}EB + T \quad (3)$$

$$\text{transalkylation: } EB + X \rightleftharpoons di\text{-}Me\text{-}EB + B \quad (4)$$

$$\text{disproportionation: } 2EB \rightleftharpoons di\text{-}EB + B \quad (5)$$

$$\text{hydrodealkylation: } EB + H_2 \rightarrow B + C_2 \quad (6)$$

$$\text{hydrocracking: } EB + H_2 \rightarrow C_1\text{-}C_6 \text{ paraffins} \quad (7)$$

EB=ethylbenzene, di-EB=diethylbenzene, Me-EB=methylethyl benzene, di-Me-EB=dimethylethylbenzene, T=toluene, B=benzene, X=xylene.

The EBR is calculated as:

$$EBR = \frac{EB \text{ (in feed)} - EB \text{ (in prod)}}{EB \text{ (in feed)}} \times 100\%$$

(c) Xylene Reduction

The xylene reduction is caused by the reactions (3) and (4) and by the two following reactions:

$$\text{disproportionation: } 2X \rightleftharpoons T + TMB \quad (8)$$

$$\text{hydrodealkylation: } X + H_2 \rightarrow T + C_1 \quad (9)$$

$$\text{hydrocracking: } X + H_2 \rightarrow C_1\text{-}C_6 \text{ paraffins} \quad (10)$$

TMB=trimethylbenzene

The xylene reduction (XR) is calculated as:

$$XR = \frac{\text{total } X \text{ (in feed)} - \text{total } X \text{ (in prod)}}{\text{total } X \text{ (in feed)}} \times 100\%$$

(d) Gasmake

This is a measure of the amount of hydrocracking and hydrodealkylation resulting from equations (6), (7), (9) and (10), and is measured in terms of the sum of wt. % of light ends ($C_1$–$C_6$ paraffins) in the product samples.

Method

The kinetic measurements were performed in a U-tube microreactor containing 5 to 10 grams of crushed catalyst pellets (20–40 mesh) containing 15% (by weight) kaolin as binding agent.

All catalysts were tested under the following conditions:

$H_2$/hydrocarbon mole ratio: 4
WHSV: 5
Pressure: 30 bar g
Temperature range: 250°–450° C.

Details of the feeds used in each test are given hereinafter.

The feed and product samples were analysed by GLC using a bentone 34/diisodecylphthalate column equipped with a Perkin Elmer AS-100 automatic sampling system. The amount and the breakdown of the gas lost via the gaspurge was determined by a Squalane capilliary column.

TEST 1

Isomerization of a meta-xylene feed

A substantially pure meta-xylene feed was isomerized under the conditions indicated above for several reactor temperatures using both catalysts of the invention and conventional catalysts. In each case the feed contained 98.8 wt. % meta-xylene.

| Results | | | | | |
|---|---|---|---|---|---|
| (a) Catalyst = Comparison I | | | | | |
| Reactor temp. (°C.) | 250 | 75 | 300 | 325 | 350 |
| XR | 0.04 | 0.12 | 0.35 | 1.2 | 3.5 |
| PX approach to eqm. | 40.5 | 82.1 | 97.3 | 98.3 | 97.3 |
| OX approach to eqm. | 7.0 | 28.8 | 61.8 | 88.8 | 95.1 |
| (b) Catalyst = Comparison II | | | | | |
| Reactor temp. (°C.) | 275 | 75 | 325 | 350 | 375 |
| XR | 0.2 | 0.2 | 0.3 | 0.9 | 2.8 |
| PX approach to eqm. | 26.6 | 57.3 | 83.9 | 96.4 | 95.3 |
| OX approach to eqm. | 7.2 | 22.0 | 49.8 | 82.2 | 96.2 |
| (c) Catalyst = Example 2 | | | | | |
| Reactor temp. (°C.) | 250 | 275 | 300 | 325 | 350 |
| XR | 0.04 | 0.12 | 0.35 | 1.18 | 3.46 |
| PX approach to eqm. | 40.1 | 81.5 | 96.9 | 97.8 | 97.2 |
| OX approach to eqm. | 7.69 | 30.8 | 64.9 | 92.5 | 97.4 |

These results show the process of the invention, using a composite catalyst having an outer shell of gallosilicate to be similar in isomerization efficiency to a process using a composite catalyst having an aluminosilicate shell, and to be more effective than processes using conventional zeolites.

TEST 2

Isomerization of EB-depleted feeds

A similar test to Test 1 was carried out, but using an EB-depleted feed containing in the region of 2 wt. % ethylbenzene, and using the catalysts of Examples 2 and 5, comparison catalyst I and silicalite.

| Results | | | |
|---|---|---|---|
| (a) Catalyst = comparison I, precalcined, $NH_4+$ exchanged and calcined 16 hours at 400| C. | | | |
| Run | A | B | C |
| 1st run: feed: non-aromatics | 0.01 | 0.01 | 0.02 |
| (wt %) benzene | 0.01 | 0.01 | — |
| toluene | 0.08 | 0.03 | 0.10 |
| ethylbenzene | 2.12 | 2.12 | 2.10 |
| para-xylene | 9.56 | 9.56 | 9.63 |
| meta-xylene | 78.1 | 78.1 | 77.71 |
| ortho-xylene | 10.0 | 10.0 | 10.38 |
| other aromatics | 0.06 | 0.06 | 0.01 |

-continued

Results:

| | | | | | |
|---|---|---|---|---|---|
| Reactor temp. (|C.) | 275 | 300 | 325 | 350 | 375 |
| RUN A: | | | | | |
| PX approach to eqm. | 77.7 | 92.1 | 98.7 | 98.4 | |
| OX approach to eqm. | 35.7 | 65.6 | 93.8 | 102 | |
| EBR | 2.83 | 9.91 | 30.7 | 67.5 | |
| XR | 0.32 | 0.71 | 1.93 | 5.16 | |
| Gasmake (wt %) | 0.015 | 0.04 | 0.120 | 0.315 | |
| RUN B: | | | | | |
| Reactor temp. (°C.) | 275 | 300 | 325 | 350 | 375 |
| PX approach to eqm. | 73.4 | 93.6 | 95.5 | 96.3 | 96.4 |
| OX approach to eqm. | 32.7 | 67.8 | 90.6 | 96.6 | 98.7 |
| EBR | 5.19 | 12.3 | 34.0 | 68.9 | 92.0 |
| XR | 0.29 | 0.71 | 2.01 | 5.4 | 12.3 |
| Gasmake (wt %) | 0.015 | 0.050 | 0.115 | 0.335 | 0.795 |
| RUN C: | | | | | |
| Gasmake (wt %) | 0.045 | 0.095 | 0.240 | 0.490 | 1.380 |

(b) Catalyst = Example 2, $NH_4+$ exchanged and calcined 16 hours at 400° C.

| feed: non-aromatics | | | 0.01 | | |
|---|---|---|---|---|---|
| (wt %) benzene | | | — | | |
| toluene | | | 0.08 | | |
| ethylbenzene | | | 2.07 | | |
| para-xylene | | | 9.58 | | |
| meta-xylene | | | 78.1 | | |
| ortho-xylene | | | 10.1 | | |
| other aromatics | | | 0.02 | | |
| Reactor temp. (°C.) | 275 | 300 | 325 | 350 | 375 | 400 |
| PX app. to eqm. | 53.2 | 86.6 | 96.7 | 96.8 | 96.9 | 97.1 |
| OX app. to eqm. | 22.1 | 54.9 | 88.2 | 97.9 | 99.2 | 99.4 |
| EBR. | 1.45 | 4.35 | 14.0 | 38.6 | 71.0 | 88.9 |
| XR | 0.65 | 1.08 | 1.31 | 2.14 | 4.79 | 9.32 |
| Gasmake (wt %) | 0.038 | 0.045 | 0.125 | 0.26 | | |

(c) Catalyst = Example 5, calcined at 475° C.

| feed: non-aromatic | | | 0.02 | | |
|---|---|---|---|---|---|
| (wt %) benzene | | | — | | |
| toluene | | | 0.1 | | |
| ethylbenzene | | | 2.03 | | |
| para-xylene | | | 9.27 | | |
| meta-xylene | | | 78.6 | | |
| ortho-xylene | | | 9.94 | | |
| other aromatics | | | 0.02 | | |
| Reactor temp. (°C.) | 275 | 300 | 325 | 350 | 375 |
| PX approach to eqm. | 16.1 | 47.4 | 76.7 | 94.8 | 96.8 |
| OX approach to eqm. | 9.64 | 29.3 | 58.6 | 83.9 | 92.9 |
| EBR | — | 0.49 | 2.96 | 9.36 | 24.1 |
| XR | 0.24 | 0.22 | 0.34 | 0.57 | 1.2 |
| Gasmake | — | 0.02 | 0.025 | 0.04 | 0.06 |

(d) Catalyst = silicalite.

| feed: non-aromatics | | | 0.01 | | | | |
|---|---|---|---|---|---|---|---|
| (wt %) benzene | | | — | | | | |
| toluene | | | 0.13 | | | | |
| ethylbenzene | | | 2.06 | | | | |
| para-xylene | | | 9.40 | | | | |
| meta-xylene | | | 78.33 | | | | |
| ortho-xylene | | | 10.05 | | | | |
| other aromatics | | | 0.02 | | | | |
| Reactor temp. (|C.) | 300 | 325 | 350 | 375 | 400 | 425 | 450 |
| PX approach to eqm. | * | * | 4.7 | 10.4 | 16.6 | 28.4 | 57.2 |
| OX approach to eqm. | * | * | 3.6 | 6.7 | 11.2 | 18.7 | 38.0 |
| EBR | * | * | * | * | * | * | 8.2 |
| XR | * | * | * | * | * | * | * |
| Gasmake | — | — | 0.025 | 0.045 | 0.035 | 0.045 | 0.075 |

* = change in product too small for percentage change to be satisfactory measure of activity.

Figure 1:
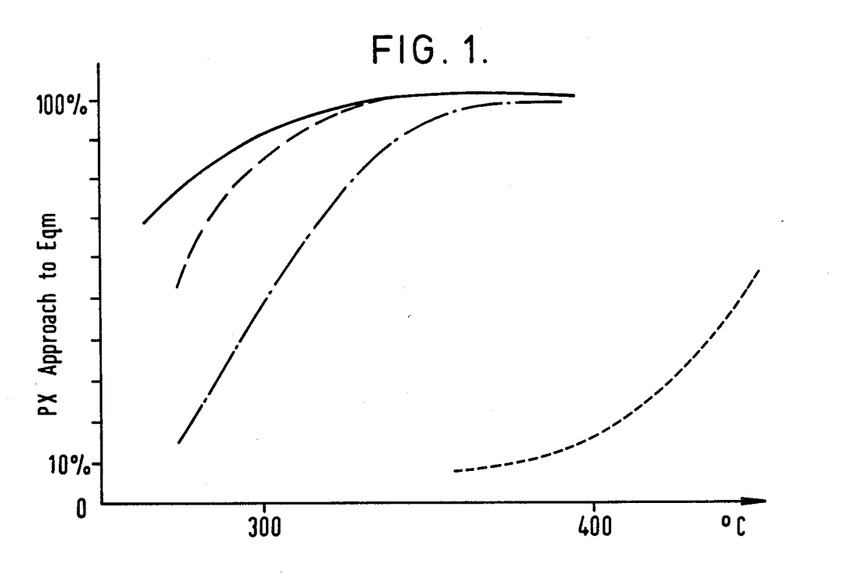
FIG. 1 is a graph showing the PX approach to equilibrium in isomerization of EB-depleted mixed xylene feeds for a variety of reactor temperatures for the catalyst of Examples 2 and 5, and for comparison catalyst I and for silicalite.
Figure 2:
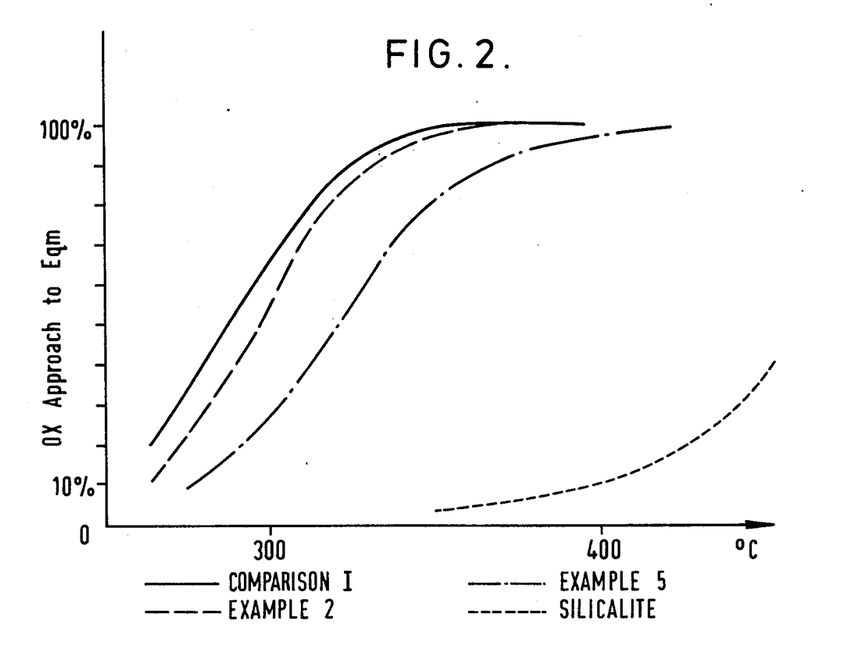
FIG. 2 is a graph showing the OX approach to equilibrium plotted against reactor temperature for the same two catalysts as in FIG. 1.

The results for PX and OX approach to equilibrium are shown in FIGS. 1 and 2. The catalyst prepared in Example 2 requires a slightly higher temperature to achieve the same degree of isomerization as the comparison catalyst I using an aluminosilicate zeolite component. However, it is pointed out that comparison catalyst I has a significantly higher metal to silicon ratio than the catalyst of Example 2, and would therefore be expected to be more active. The surprising aspect of the results is that the catalyst of Example 2 shows significantly less downgrading to $C_1$-$C_6$ paraffins caused by hydrocracking of the aromatic species, even when the catalyst of Example 2 and comparison catalyst I are compared at the temperatures at which they show similar activity.

The results for the catalyst prepared in Example 5 show that lowering the gallium content leads to a fall in xylene isomerization activity of the catalyst, but also an extremely marked reduction in downgrading to $C_1$-$C_6$ paraffins, so that it is possible to use the catalyst at higher temperatures to attain a greater degree of xylene isomerization and yet still suffer less downgrading than with an alumino-silicate zeolite catalyst.

The results for the silica polymorph "Silicalite" clearly demonstrate that this material alone does not possess the advantages of the composite catalysts preferably used in the invention. At 450° C. the degree of xylene isomerization is low, much lower than that attained using the catalyst of Example 5 at 325° C. or the catalyst of Example 2 at 300° C., and silicalite gives a higher degree of downgrading at 450° C. than the composite catalysts at 325° C. and 300° C. respectively.

We claim:

1. A process for obtaining ethylbenzene and para-xylene and/or ortho-xylene from a mixed $C_8$ feed, which process comprises recovering ethylbenzene from the mixed $C_8$ feed to leave an ethylbenzene-depleted feed containing mixed xylenes and less than 5 wt.% ethylbenzene, thereafter contacting the ethylbenzene-depleted feed under isomerization conditions with a catalyst comprising a gallosilicate zeolite having a mole ratio of $SiO_2:Ga_2O_3$ greater than 5 and a consistent index of from 1 to 12, said gallosilicate zeolite overlying a silica core, the silica core and the zeolite having substantially the same crystalline structure, to give an isomerate enriched in para-xylene and ortho-xylene, and recovering para-xylene and/or ortho-xylene from the isomerate which is thereafter recycled to the ethylbenzene recovery step.

2. A process as claimed in claim 1, in which the mean ratio of silicon to gallium (expressed in terms of mole ratios of their oxides) is from 20 to 500.

3. A process as claimed in claim 1, in which the silica core has a crystallite size of greater than $0.1\mu$ mean diameter.

4. A process as claimed in claim 1, in which the weight ratio of the silica core to the overlying gallosilicate zeolite (expressed in terms of the weight ratio of the $SiO_2$ core to the $SiO_2$ in the reaction mixture for the modified-silica) is from 1:1 to 10:1.

5. A process as claimed in claim 4, in which the weight ratio of the silica core to the overlying zeolite is from 1:1 to 4:1.

6. A process as claimed in claim 1 in which the zeolite and the core have an X-ray diffraction pattern showing the lines characteristic of the d spacings of ZSM-5.

* * * * *